(12) United States Patent
Erez (10) Patent No.: US 10,740,345 B2
(45) Date of Patent: Aug. 11, 2020

(54) DATA STRUCTURES FOR STORING AND MANIPULATING LONGITUDINAL DATA AND CORRESPONDING NOVEL COMPUTER ENGINES AND METHODS OF USE THEREOF

(71) Applicant: Luz Erez, Meitar (IL)

(72) Inventor: Luz Erez, Meitar (IL)

(73) Assignee: MDClone Ltd., Beer-Sheva (IL)

( * ) Notice: Subject to any disclaimer, the term of this patent is extended or adjusted under 35 U.S.C. 154(b) by 0 days.

(21) Appl. No.: 16/454,639

(22) Filed: Jun. 27, 2019

(65) Prior Publication Data

US 2020/0004755 A1  Jan. 2, 2020

Related U.S. Application Data

(60) Provisional application No. 62/690,647, filed on Jun. 27, 2018.

(51) Int. Cl.
| | |
|---|---|
| *G06F 16/00* | (2019.01) |
| *G06F 16/25* | (2019.01) |
| *G16H 10/60* | (2018.01) |
| *G06F 16/2458* | (2019.01) |
| *G06F 16/22* | (2019.01) |
| *G06F 16/36* | (2019.01) |
| *G06F 16/28* | (2019.01) |
| *G06F 16/31* | (2019.01) |

(52) U.S. Cl.
CPC ............ *G06F 16/252* (2019.01); *G06F 16/22* (2019.01); *G06F 16/2228* (2019.01); *G06F 16/2477* (2019.01); *G06F 16/284* (2019.01); *G06F 16/285* (2019.01); *G06F 16/316* (2019.01); *G06F 16/367* (2019.01); *G16H 10/60* (2018.01)

(58) Field of Classification Search
CPC ........ G16H 50/20; G16H 50/70; G16H 10/60; G16H 10/20; G06F 16/367; G06F 16/22; G06F 16/285; G06F 16/282; G06F 16/316; G06F 19/36; G06Q 50/24
See application file for complete search history.

(56) References Cited

U.S. PATENT DOCUMENTS

| | | | | |
|---|---|---|---|---|
| 5,924,074 | A * | 7/1999 | Evans | .................... G06F 19/325 705/3 |
| 7,885,822 | B2 * | 2/2011 | Akers | .................. G06F 19/3418 705/2 |

(Continued)

*Primary Examiner* — Srirama Channavajjala
(74) *Attorney, Agent, or Firm* — Greenberg Traurig, LLP (57) ABSTRACT

In some embodiments, the present disclosure provides for an exemplary computer-implemented system that may include a longitudinal data engine, including: a processor and specialized index generation software to generate: an index data structure for a respective event type associated with each respective subject or object; where each respective index data structure is a respective event type-specific data schema, defining how to store events of a particular event type to form longitudinal data of each respective subject or object; an ontology data structure that is configured to describe one or more properties of a respective event of a respective subject or object; and longitudinal data extraction software to extract a respective longitudinal data for a plurality of index data structures and a plurality of ontology data structures associated with a plurality of subjects or objects.

12 Claims, 4 Drawing Sheets

(56) References Cited

U.S. PATENT DOCUMENTS

| | | | | |
|---|---|---|---|---|
| 8,429,179 B1* | 4/2013 | Mirhaji | ............... | G06F 17/274 |
| | | | | 707/756 |
| 10,347,370 B1* | 7/2019 | Kim | ............... | G06F 16/2477 |
| 2003/0208382 A1* | 11/2003 | Westfall | ............... | G16H 10/65 |
| | | | | 705/3 |
| 2004/0122706 A1* | 6/2004 | Walker | ............... | G06F 19/324 |
| | | | | 705/2 |
| 2005/0034107 A1* | 2/2005 | Kendall | ............... | G06N 5/027 |
| | | | | 717/136 |
| 2007/0094188 A1* | 4/2007 | Pandya | ............... | G16H 50/20 |
| | | | | 706/45 |
| 2012/0330875 A1* | 12/2012 | Angele | ............... | G06N 5/025 |
| | | | | 706/47 |
| 2012/0330974 A1* | 12/2012 | Zillner | ............... | G06F 16/367 |
| | | | | 707/749 |
| 2014/0365210 A1* | 12/2014 | Riskin | ............... | G06F 17/2765 |
| | | | | 704/9 |
| 2015/0142821 A1* | 5/2015 | Rassen | ............... | G06F 16/316 |
| | | | | 707/742 |
| 2016/0019299 A1* | 1/2016 | Boloor | ............... | G06F 16/9535 |
| | | | | 705/3 |
| 2017/0185674 A1* | 6/2017 | Tonkin | ............... | G06F 16/328 |

* cited by examiner

DATA STRUCTURES FOR STORING AND MANIPULATING LONGITUDINAL DATA AND CORRESPONDING NOVEL COMPUTER ENGINES AND METHODS OF USE THEREOF

CROSS-REFERENCE TO RELATED APPLICATIONS

This application claims benefit of U.S. provisional patent application Ser. No. 62/690,647 filed Jun. 27, 2018, which is herein incorporated by reference for all purposes.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in drawings that form a part of this document: Copyright, MDClone Ltd., All Rights Reserved.

BACKGROUND

As detailed herein, typically, electronic data records on a population of real individuals may have one or personal identifying attributes (identification identifiers), such as, but not limited to, names, birthdays, ages, addresses, zip codes, social security numbers; phones, etc. For example, a cable company may track records of personal viewing preferences together personal identifying information of its subscribers (identification identifiers). In another example, an internet company may track internet activity of its users together with personal identifying information. For example, a typical source electronic medical record (EMR) data object is a collection of electronic health information about an individual or a population of individuals. A typical source EMR data object includes record(s) in digital format that is/are capable of being shared across different healthcare settings. A typical source EMR data object may include record(s) with categorical/discrete/qualitative and/or quantitative data which are representative of individual identifiable information, individual health/medical information, doctors visit information, prescriptions, service providers information (e.g., MRI provider, etc.), test results information (e.g., numerical values), and other similarly suitable information.

SUMMARY OF THE DISCLOSURE

In some embodiments, the present disclosure provides for an exemplary computer-implemented system that may include at least the following components: at least one longitudinal data engine, including: at least one processor; specialized index generation software; where, when executing the specialized index generation software, the at least one processor at least generates: i) at least one index data structure for a respective event type associated with each respective subject or object; where each respective index data structure is a respective event type-specific data schema, defining how to store events of a particular event type to form longitudinal data of each respective subject or object; ii) at least one ontology data structure that is configured to describe one or more properties of a respective event of a respective subject or object; and longitudinal data extraction software; where, when executing the longitudinal data extraction software, the at least one processor extract a respective longitudinal data for a plurality of index data structures and a plurality of ontology data structures associated with a plurality of subjects or objects, by at least: i) receiving at least one electronic query that at least identifies: 1) one of more characteristics of the particular population of subjects or objects, and 2) at least one particular event of at least one particular event type; ii) extracting, based on the at least one electronic query, a plurality of population-specific index data structures of the particular population of subjects or objects; iii) searching the plurality of population-specific index data structures of the particular population of subjects or objects to identify at least one ontology associated with the at least one particular event of each particular subject or object of the particular population of subjects or objects to form a plurality of longitudinal-personalized data extracts of the at least one particular event of the particular population of subjects or objects; and iv) generating at least one interactive chronological timeline for each subject or object of the particular population of subjects or objects based at least in part on the plurality of longitudinal-personalized data extracts of the at least one particular event of the particular population of subjects or objects.

In some embodiments, the present disclosure provides for an exemplary computer-implemented method that may include at least the following: generating, by at least one processor, at least: i) at least one index data structure for a respective event type associated with each respective subject or object; where each respective index data structure is a respective event type-specific data schema, defining how to store events of a particular event type to form longitudinal data of each respective subject or object; ii) at least one ontology data structure that is configured to describe one or more properties of a respective event of a respective subject or object; and extracting, by at least one processor, a respective longitudinal data for a plurality of index data structures and a plurality of ontology data structures associated with a plurality of subjects or objects, by at least: i) receiving at least one electronic query that at least identifies: 1) one of more characteristics of the particular population of subjects or objects, and 2) at least one particular event of at least one particular event type; ii) extracting, based on the at least one electronic query, a plurality of population-specific index data structures of the particular population of subjects or objects; iii) searching the plurality of population-specific index data structures of the particular population of subjects or objects to identify at least one ontology associated with the at least one particular event of each particular subject or object of the particular population of subjects or objects to form a plurality of longitudinal-personalized data extracts of the at least one particular event of the particular population of subjects or objects; and iv) generating at least one interactive chronological timeline for each subject or object of the particular population of subjects or objects based at least in part on the plurality of longitudinal-personalized data extracts of the at least one particular event of the particular population of subjects or objects.

In some embodiments, the at least one index data structure is a cohort index data structure.

In some embodiments, when executing the specialized index generation software, the at least one processor further generates the at least one index data structure by utilizing structure hierarchical data elements of a hierarchical data format.

In some embodiments, the at least one ontology data structure is nested within the at least one index data structure. In some embodiments, each property of a plurality of properties of a particular ontology data structure of the respective event are separated by a pre-determined delineator.

In some embodiments, when executing the longitudinal data extraction software, the at least one processor further distributes the plurality of population-specific index data structures of the particular population of subjects or objects into a plurality of searching cluster nodes for searching to identify the at least one ontology associated with the at least one particular event of each particular subject or object of the particular population of subjects or objects to form the plurality of longitudinal-personalized data extracts of the at least one particular event.

In some embodiments, where, when executing the longitudinal data extraction software, the at least one processor further generates the at least one interactive chronological timeline for each subject or object of the particular population of subjects or objects based on the plurality of longitudinal-personalized data extracts of the at least one particular event of the particular population of subjects or objects and at least one reference event.

In some embodiments, the at least one electronic query further identifies the at least one reference event; and a date of the at least one reference event defines a reference date for the extracting, based on the at least one electronic query, the plurality of population-specific index data structures of the particular population of subjects or objects.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION OF EXEMPLARY EMBODIMENTS

Among those benefits and improvements that have been disclosed, other objects and advantages of this disclosure can become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the disclosure may be readily combined, without departing from the scope or spirit of the disclosure.

In addition, as used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred (e.g., less than 1 second difference between sequential events/actions).

As used herein, the term "dynamic(ly)" means that events and/or actions can be triggered and/or occur without any human intervention.

As used herein, the term "computer engine" identifies at least one software component and/or a combination of at least one software component and at least one hardware component which are designed/programmed/configured to manage/control other software and/or hardware components (such as the libraries, software development kits (SDKs), objects, etc.).

In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, etc.

In some embodiments, the inventive adaptive self-trained computer engines with associated devices may be configured to operate in the distributed network environment, communicating over a suitable data communication network (e.g., the Internet, etc.) and utilizing at least one suitable data communication protocol (e.g., IPX/SPX, X.25, AX.25, AppleTalk™, TCP/IP (e.g., HTTP), etc.). Of note, the embodiments described herein may, of course, be implemented using any appropriate hardware and/or computing software languages. In this regard, those of ordinary skill in the art are well versed in the type of computer hardware that may be used, the type of computer programming techniques that may be used (e.g., object oriented programming), and the type of computer programming languages that may be used (e.g., C++, Basic, AJAX, Javascript). The aforementioned examples are, of course, illustrative and not restrictive.

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor.

In one example implementation, a multi-processor system may include a plurality of processor chips each of which includes at least one I/O component. Each of the processor chips may also include a voltage regulation circuit configured to regulate a voltage of one or more of the processor chips. In some embodiments, the voltage regulation circuit of each of the processor chips may provide one or more voltage domains of the respective processor chip. In some embodiments, the multi-processor system may further include one or more additional electronic components, e.g., inductors, as part of the package. In some embodiments, the multi-processor system may include at least 10,000 processor chips. In some embodiments, a density of the processor chips may be greater than 1,000 chips per cubic meter. In some embodiments, a latency of the multi-processor system, having more than 1,000 processor chips, may be less than 200 nanoseconds (ns).

In one example implementation, a multi-processor system may include an inter-processor interconnect (IPI) and a plurality of processor chips. The processor chips are configured to communicate data to one another through the IPI. Each of the processor chips may include one or more cores and one or more level 1 (L1) caches. Each of the L1 caches may be associated with a respective core through a respective core-cache bandwidth. Each of the processor chips may also include at least one memory controller and one or more local memory devices. Each of the local memory devices may be associated with the at least one memory controller through a respective local memory bandwidth. Each of the processor chips may further include an on-chip interconnect (OCI) that is associated with the one or more cores and the at least one memory controller of that processor chip. The OCI is also associated with the IPI of the multi-processor system. The association between the OCI and the plurality of cores of that processor chip is through a bandwidth that is greater than 50% of an aggregate core bandwidth, which is approximately the sum of each core-cache bandwidth of that processor chip. The association between the OCI and the at least one memory controller of that processor chip is through a bandwidth that is greater than 50% of an aggregate memory bandwidth, which is approximately the sum of each local memory bandwidth of that processor chip. The association between the OCI and the IPI of the multi-processor system is through an injection bandwidth. In some embodiment, the injection bandwidth is greater than 50% of the aggregate core bandwidth of that processor chip. In some embodiment, the injection bandwidth is greater than 50% of a sum of the aggregate core bandwidth and the aggregate memory bandwidth of that processor chip.

In some embodiments, a plurality of concurrent users can be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-10,000,000,000).

As referenced herein, the terms "personal event," "patient event," "user event," "patient event of interest," and "user event of interest" are interchangeably used and identify a particular life event of an individual. In some embodiments, the particular life event may be healthcare-related (e.g., doctor visit). In some embodiments, the particular life event may be non-healthcare-related. For example, an exemplary user event may be any one of the following, but not limited to: a medical procedure, an image (e.g., X-ray or MRI image), a drug, a prescription, a laboratory result, etc.

For example, a typical source EMR dataset can have at least 1,000 to 1,000,000 rows and at least 50 to 1,000 columns. For example, a typical source EMR dataset can have at least 10,000 to 1,000,000 rows and at least 100 to 2,000 columns. For example, a typical source EMR dataset can have at least 1,000 to 10,000,000 rows and at least 50 to 3,000 columns. For example, a typical source EMR dataset can have at least 10,000 to 1,000,000,000 rows and at least 50 to 3,000 columns. For example, a typical source EMR dataset can have at least 1,000 rows and at least 50 columns. For example, a typical source EMR dataset can have at least 10,000 rows and at least 100 columns. For example, a typical source EMR dataset can have at least 1,000,000 rows and at least 100 columns. For example, a typical source EMR dataset can have at least 1,000 rows and at least 1,000 columns. For example, a typical source EMR dataset can have at least 10,000 rows and at least 2,000 columns. For example, a typical source EMR dataset can have at least 1,000,000 rows and at least 2,000 columns.

In some embodiments, the present disclosure provides for various computer engines that may be configured/programmed to generate and/or maintain database(s) for storing and manipulating longitudinal data. Typically, the term "longitudinal data" may be referred to as panel data, allowing to track the same sample (e.g., a population sample) at different points in time, by allowing the measurement of the duration of events, and record the timing of various events. For example, in case of clinical data, an exemplary sample may include individuals, events, repeated cross-sectional data, long-term data, and other similar type of data. For example, longitudinal data can be the weight of a person which may fluctuate over a lifetime. Using this longitudinal data, a histogram of a person's weight over time displays periods of being underweight, normal weight, and over-weight. Yet another example, suppose the unemployment rate remained high for a long period of time, one may use longitudinal data to determine if the same group of individuals stays healthy over the entire period or if different groups of individuals move in and out of the healthy state over the time period.

Yet another example, an exemplary inventive longitudinal data engine with an associated exemplary inventive longitudinal database may be configured, for example without limitation, to provide responses to inquiries such as: "For a person in the intensive care unit (ICU) with hypoalbuminemia situation in the 48 hours prior to hospitalization what type of drug would reduce the probability for hypoglycemia event(s) in the next 72 hours?" Typically, an answer to such single question would require numerous database inquiries and programming one or more specialized stored procedures using a standard relational database approach. For example, typically, the standard relational database approach needs to define primary keys and foreign keys. In turn, typically, when records are created in a relational database for several sequential events in a patient life, such events would be recorded in records among numerous tables and rows. Further, typically, such tables would have data for numerous patients. Typically, complex querying code would need to be programmed (e.g., utilizing numerous SQL commands) to isolate sequential events of a single patient which is typically inefficient (time consuming) and, in many cases, not practical (e.g., requiring specialized programming resources).

In some embodiments, the present disclosure provides for an exemplary inventive longitudinal data engine that is associated with an exemplary inventive two-stage data structure arrangement. In some embodiments, the exemplary inventive longitudinal data engine of the present disclosure is configured to include at least:

1) a specialized index structure generation module that may be configured to utilize data structures such as, but without limitation, a cohort index that is a tabular structure configured to allow to identify a desired population (e.g., a population of living subjects (e.g., people (e.g., patients), animals, etc.), a population of objects (e.g., cars, factories, etc.); and 2) a specialized extraction framework module that may utilize a time-based structure that may be configured to allow to extract temporal data (sequential events data) for a selected population.

In some embodiments, the associated exemplary inventive two-stage data storing schema may be designed to include at least:

1) a first structure of a corresponding specialized index structure (e.g., cohort index structure), and 2) a second structure that stores corresponding ontology for each subject or object.

While it is understood that the present disclosure should not be limited to specific examples/embodiments detailed herein, for illustrative purposes only, the exemplary inventive longitudinal data engine with the associated exemplary inventive two-stage data storing schema may be further illustrated in relation to healthcare, clinical data for a population of patients.

In some embodiments, in accordance with the associated exemplary inventive two-stage data storing schema, the exemplary clinical data for the exemplary population of patients is duplicated in both of the structures (i.e., the corresponding cohort index structure and ontologies-storing structure) with different internal representation. In some embodiments, the corresponding cohort index structure is designed as an event-based tabular structure where each event type is represented by a particular data schema (e.g., table). For example, an exemplary event type table may include, for every patient, 1) required field(s) such as a personal unique identifier (e.g., "Patient ID" of Table 1) and a timestamp (e.g., "Time of intake" of Table 1), and 2) one or more other relevant data property(ies), as, for example, without limitation, properties illustratively identified in Table 1 for the event type of medication intake.

TABLE 1

| Field | Data sample |
|---|---|
| PatientID | 12336678 |
| Time of intake | Jan. 3, 1998 |
| Medication Name | Aspirin |
| Dosage | 100 Mg |
| Manufacturer | Teva |

In some embodiments, the exemplary inventive ontologies-storing structure includes one or more ontologies that can describe one or more respective properties of the particular event type. As illustrated in Table 2, for example, a field "medication code" may be followed by a field of "medication code ontology" containing one or more descriptive ontological variables separated by one or more particular delineators (e.g., symbols (e.g., "#"), characters, etc.).

TABLE 2

| Field | Data sample |
|---|---|
| PatientID* | 12336678 |
| Time of intake* | Jan. 3, 1998 |
| Medication Name | Aspirin |
| Medication Code | 2334519 |
| Medication Code Ontology | NSAID # Pain Relief # acetylsalicylic acid # Bayer Aspirin |
| Dosage | 100 Mg |
| Manufacturer | Teva |

In some embodiments, similar data structures having at least the cohort index structure and the ontologies-storing structure may be designed for every type of patient events (e.g., procedures, encounters, surgeries, imaging, diagnostics, demographics, etc.)

Figure 1:
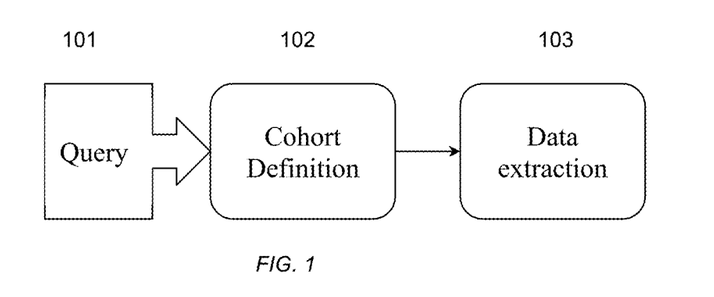
FIGS. 1-5 are representative of some exemplary aspects of the present disclosure in accordance with at least some principles of at least some embodiments of the present disclosure.
Figure 2:
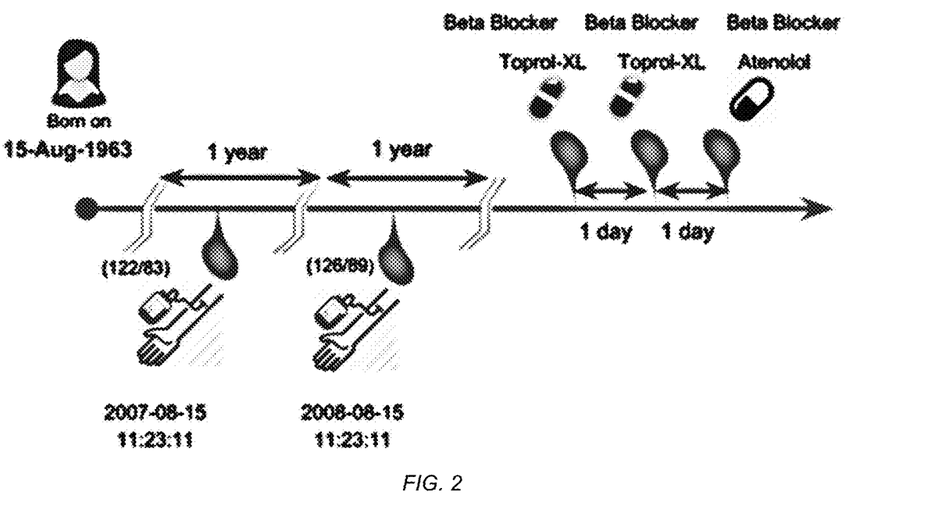

In some embodiments, the exemplary inventive longitudinal data engine is configured based on an exemplary inventive extraction framework that can be constructed from a collection of data structures. For example, the exemplary inventive longitudinal data engine may include a separate data structure generated for each object/subject (e.g., every patient). In some embodiments, the exemplary inventive separate data structures can be configured to hold, for each object/subject (e.g., every patient), events sorted by time so as to allow to cause the exemplary inventive longitudinal data engine to generate visual representation that longitudinally tracks events over a period of time as, for example, without limitation, illustrated in FIG. 2. Referring to FIG. 2, the exemplary inventive separate data structures can be configured to store for every event at least:

1) a timestamp,
2) every property value,
3) time period(s) passed between similar event(s) (e.g., blood tests), and
4) time period(s) passed between similar ontology properties (e.g., medications).

In some embodiments, the exemplary inventive separate data structures can be generated utilizing structure hierarchical data elements such as, without limitation, XML, JSON, and similar others. Table 3 provides an exemplary inventive separate data structure designed in XML format.

TABLE 3

```
<Patient ID="1234" BirthDate="1963-08-15">
  <Event Type="BloodPressure" TimeOfEvent="2007-08-15 11:23:11"
HourToNext="8760">
    <SystolicPressure>122</SystolicPressure>
    <DiastolicPressure>83<DiastolicPressure/>
  <Event>
<Event Type="BloodPressure" TimeOfEvent="2008-08-15 11:23:11"
HourToNext="">
    <SystolicPressure>126</SystolicPressure>
    <DiastolicPressure>89<DiastolicPressure/>
  <Event>
<Event Type="DrugIntake" TimeOfEvent="2009-08-15 11:23:11"
HourToNext="24">
    <DrugCode HourToNext="24">Toprol-XL</DrugCode>
    <Ontologies>
    <DrugType HourToNext="24">BetaBlocker</DrugType>
    <Intake HourToNext="24">Pill</Intake>
  <Ontologies>
<Prescriber HourToNext="24">Dr Jon Smith</Prescriber>
</Event>
<Event Type="DrugIntake" TimeOfEvent="2009-08-16 11:23:11"
HourToNext="">
    <DrugCode HourToNext="">Toprol-XL</DrugCode>
    <Ontologies>
    <DrugType HourToNext="24">BetaBlocker</DrugType>
    <Intake HourToNext="24">Pill</Intake>
  <Ontologies>
<Prescriber HourToNext="">Dr Jon Smith </Prescriber>
</Event>
<Event Type="DrugIntake" TimeOfEvent="2009-08-17 11:23:11"
HourToNext="">
    <DrugCode HourToNext="">Atenolol</DrugCode>
    <Ontologies>
    <DrugType HourToNext="">BetaBlocker</DrugType>
    <Intake HourToNext="">Pill</Intake>
  <Ontologies>
<Prescriber HourToNext="">Dr Max Lincoln </Prescriber>
</Event>
</Patient>
```

In some embodiments, the exemplary inventive longitudinal data engine is configured to extract longitudinal data (e.g., the longitudinal clinical data) from the associated exemplary inventive longitudinal database in several stages.

Exemplary First Stage

In some embodiments, at an exemplary first data extraction stage, the exemplary inventive longitudinal data engine is configured to receive a longitudinal query for one or more subjects and/or objects. Then, the exemplary inventive longitudinal data engine is configured to define, utilizing, for example without limitation, one or more SQL-like statements, a population (e.g., relevant subject(s)/object(s)) (item 301 of FIG. 3) and a cohort index structure, as illustrated in Table 3.

TABLE 3

Example 1
Select PatientsID from Patients
Where Patient.Gender='Female'
Example 2
SELECT p.`birthdate`,
    p.`gender`,
    p.`race`,
    p.`internalpatientid`,
    row_number( )
FROM `ev_demographics_static` AS p
WHERE p.`gender` = 'male'
    and p.`birthdate` > '2001-03-12'
    and p.`race` = 'asian'

Figure 4:
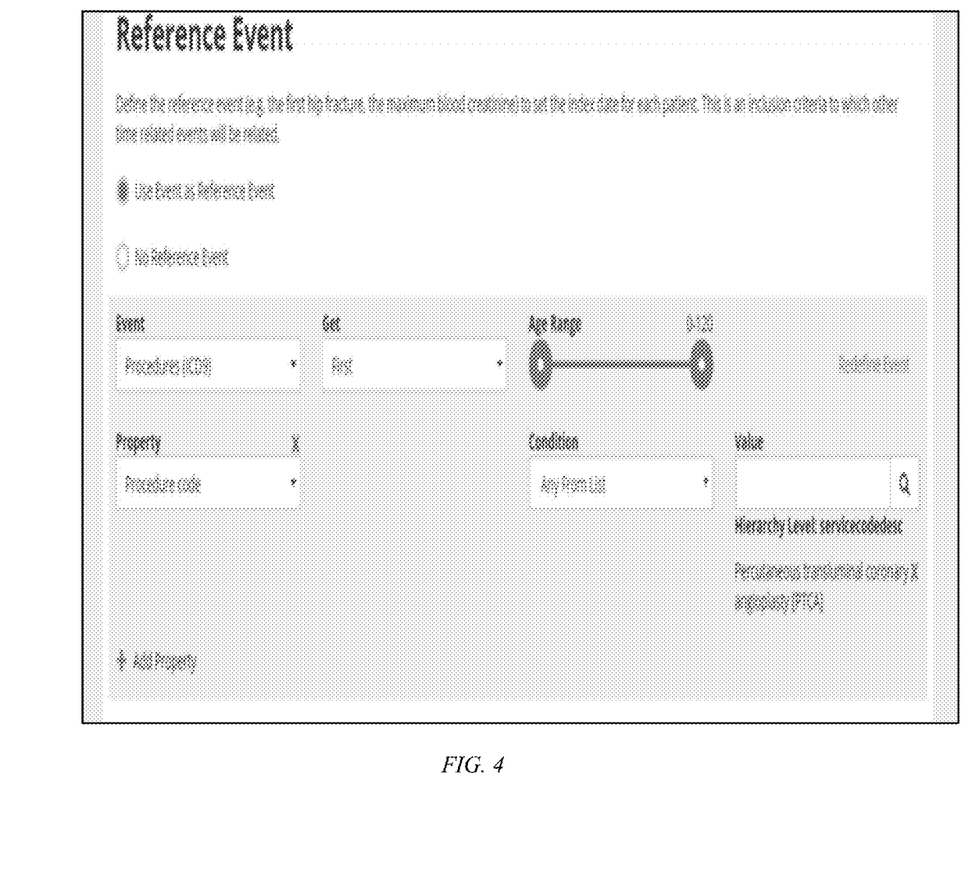

FIG. 4 is a snapshot of a computer screen that is configured to be utilized by a user to provide the exemplary inventive longitudinal data engine with parameters to define the exemplary cohort (population) from the exemplary cohort index structure. For example, FIG. 4, shows how the user may submit a query to extract from the exemplary inventive cohort index structure a particular cohort (population) having at least one (1) ontological value of percutaneous transluminal coronary angioplasty (PTCA), and for every one of identified subjects (patients) to pick an age at which first PTCA occurred (e.g., between the age 0 and 120).

Exemplary Second Stage

In some embodiments, at an exemplary second data extraction stage, the exemplary inventive longitudinal data engine is configured to extracts, for example, without limitation, XML/JSON files of the relevant subject(s)/object(s) from the exemplary inventive separate data structure.

Exemplary Third Stage

Figure 3:
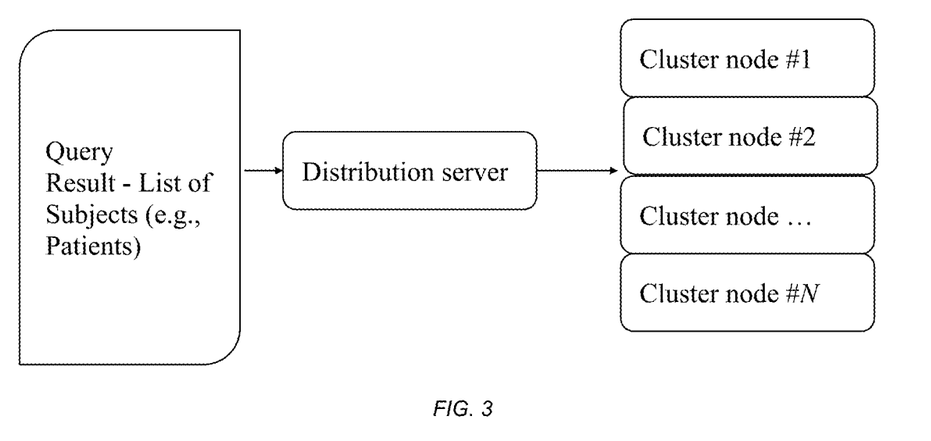

In some embodiments, at an exemplary third data extraction stage, the exemplary inventive longitudinal data engine is configured to distribute the extracted XML/JSON files of the relevant subject(s)/object(s) into a cluster of XML/JSON files (303) (searching cluster nodes), as illustrated in FIG. 3. For example, a cluster node that has received the current lowest load would be designated to perform the processing job.

Exemplary Fourth Stage

In some embodiments, at an exemplary fourth data extraction stage, the exemplary inventive longitudinal data engine is configured to scan the cluster nodes of the extracted XML/JSON files of the relevant subject(s)/object(s) to identify the desired longitudinal data by using methods such as, without limitation, XPath over XML or any other similarly suitable techniques. Then, the exemplary inventive longitudinal data engine is configured to extract the identified longitudinal data. For example, the exemplary inventive longitudinal data engine is configured to pass every cluster node once on every subject (e.g., patient) file in the defined cohort in order to identify potential answer to any question.

In some embodiments, the exemplary inventive longitudinal data engine is configured to determine the continuity or the absence of any event relay based on an accumulation of, for example, without limitation, the distinct "HourToNext" data elements.

Figure 5:
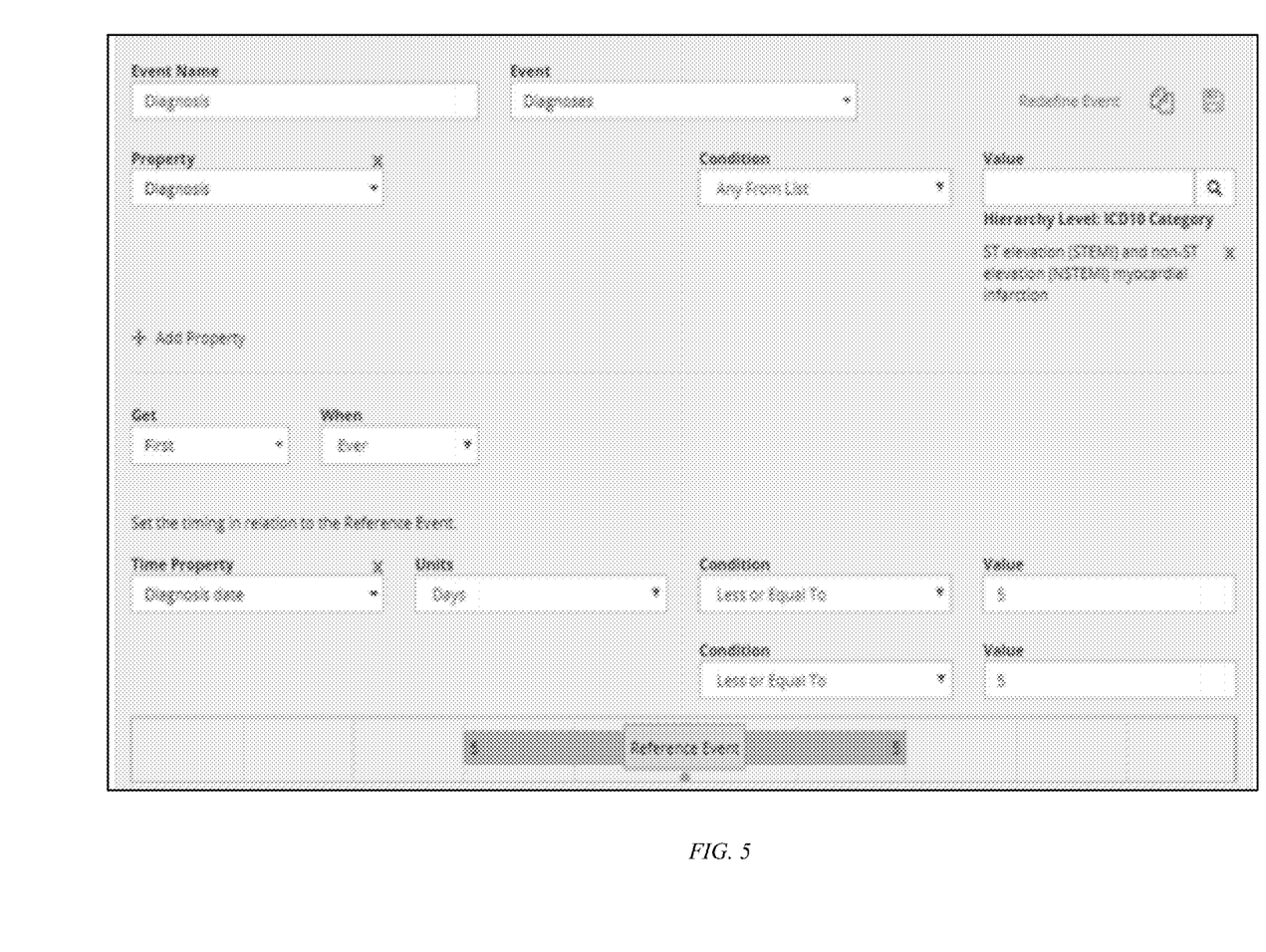

FIG. 5 illustrates a snapshot of an exemplary control interface that can allow the user to control how the exemplary inventive longitudinal data engine would scan the cluster nodes. For example, via FIG. 5, the user can set parameters that the exemplary inventive longitudinal data engine would move a particular cluster node 5 days before and after the first PTCA and look for ontology(ies) of ST elevation (STEMI) and non-ST elevation (NSTEMI) myocardial infarction.

Exemplary Fifth Stage

In some embodiments, at an exemplary fifth data extraction stage, the exemplary inventive longitudinal data engine is configured to consolidate the extracted longitudinal data for the cohort (population) to produce a respective output that may be used to generate interactive chronological timeline(s) for each subject or object.

As detailed herein, typically, electronic data records on a population of real individuals may have one or personal identifying attributes (identification identifiers), such as, but not limited to, names, birthdays, ages, addresses, zip codes, social security numbers; phones, etc. For example, a cable company may track records of personal viewing preferences together personal identifying information of its subscribers (identification identifiers). In another example, an internet company may track internet activity of its users together with personal identifying information. For example, a typical source electronic medical record (EMR) data object is a collection of electronic health information about an individual or a population of individuals. A typical source EMR data object includes record(s) in digital format that is/are capable of being shared across different healthcare settings. A typical source EMR data object may include record(s) with categorical/discrete/qualitative and/or quantitative data which are representative of individual identifiable information, individual health/medical information, doctors visit information, prescriptions, service providers information (e.g., MRI provider, etc.), test results information (e.g., numerical values), and other similarly suitable information.

In some embodiments, the present disclosure provides for an exemplary computer-implemented system that may include at least the following components: at least one longitudinal data engine, including: at least one processor; specialized index generation software; where, when executing the specialized index generation software, the at least one processor at least generates: i) at least one index data structure for a respective event type associated with each respective subject or object; where each respective index data structure is a respective event type-specific data schema, defining how to store events of a particular event type to form longitudinal data of each respective subject or object; ii) at least one ontology data structure that is configured to describe one or more properties of a respective event of a respective subject or object; and longitudinal data extraction software; where, when executing the longitudinal data extraction software, the at least one processor extract a respective longitudinal data for a plurality of index data structures and a plurality of ontology data structures associated with a plurality of subjects or objects, by at least: i) receiving at least one electronic query that at least identifies: 1) one of more characteristics of the particular population of subjects or objects, and 2) at least one particular event of at least one particular event type; ii) extracting, based on the at least one electronic query, a plurality of population-specific index data structures of the particular population of subjects or objects; iii) searching the plurality of population-specific index data structures of the particular population of subjects or objects to identify at least one ontology associated with the at least one particular event of each particular subject or object of the particular population of subjects or objects to form a plurality of longitudinal-personalized data extracts of the at least one particular event of the particular population of subjects or objects; and iv) generating at least one interactive chronological timeline for each subject or object of the particular population of subjects or objects based at least in part on the plurality of longitudinal-personalized data extracts of the at least one particular event of the particular population of subjects or objects.

In some embodiments, the present disclosure provides for an exemplary computer-implemented method that may include at least the following: generating, by at least one processor, at least: i) at least one index data structure for a respective event type associated with each respective subject or object; where each respective index data structure is a respective event type-specific data schema, defining how to store events of a particular event type to form longitudinal data of each respective subject or object; ii) at least one ontology data structure that is configured to describe one or more properties of a respective event of a respective subject or object; and extracting, by at least one processor, a respective longitudinal data for a plurality of index data structures and a plurality of ontology data structures associated with a plurality of subjects or objects, by at least: i) receiving at least one electronic query that at least identifies: 1) one of more characteristics of the particular population of subjects or objects, and 2) at least one particular event of at least one particular event type; ii) extracting, based on the at least one electronic query, a plurality of population-specific index data structures of the particular population of subjects or objects; iii) searching the plurality of population-specific index data structures of the particular population of subjects or objects to identify at least one ontology associated with the at least one particular event of each particular subject or object of the particular population of subjects or objects to form a plurality of longitudinal-personalized data extracts of the at least one particular event of the particular population of subjects or objects; and iv) generating at least one interactive chronological timeline for each subject or object of the particular population of subjects or objects based at least in part on the plurality of longitudinal-personalized data extracts of the at least one particular event of the particular population of subjects or objects.

In some embodiments, the at least one index data structure is a cohort index data structure.

In some embodiments, when executing the specialized index generation software, the at least one processor further generates the at least one index data structure by utilizing structure hierarchical data elements of a hierarchical data format.

In some embodiments, the at least one ontology data structure is nested within the at least one index data structure.

In some embodiments, each property of a plurality of properties of a particular ontology data structure of the respective event are separated by a pre-determined delineator.

In some embodiments, when executing the longitudinal data extraction software, the at least one processor further distributes the plurality of population-specific index data structures of the particular population of subjects or objects into a plurality of searching cluster nodes for searching to identify the at least one ontology associated with the at least one particular event of each particular subject or object of the particular population of subjects or objects to form the plurality of longitudinal-personalized data extracts of the at least one particular event.

In some embodiments, where, when executing the longitudinal data extraction software, the at least one processor further generates the at least one interactive chronological timeline for each subject or object of the particular population of subjects or objects based on the plurality of longitudinal-personalized data extracts of the at least one particular event of the particular population of subjects or objects and at least one reference event.

In some embodiments, the at least one electronic query further identifies the at least one reference event; and a date of the at least one reference event defines a reference date for the extracting, based on the at least one electronic query, the plurality of population-specific index data structures of the particular population of subjects or objects.

While a number of embodiments of the present disclosure have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

The invention claimed is:

1. A system comprising:
   at least one longitudinal data engine, comprising:
   at least one processor;
   specialized index generation software;
      wherein, when executing the specialized index generation software, the at least one processor at least generates:
      i) at least one index data structure for a respective event type associated with each respective subject or object;
         wherein each respective index data structure is a respective event type-specific data schema, defining how to store events of a particular event type to form longitudinal data of each respective subject or object; and
      ii) at least one ontology data structure that is configured to describe one or more properties of a respective event of a respective subject or object;
         wherein the at least one ontology data structure is nested within the at least one index data structure; and
   longitudinal data extraction software;
      wherein, when executing the longitudinal data extraction software, the at least one processor extract a respective longitudinal data for a plurality of index data structures and a plurality of ontology data structures associated with a plurality of subjects or objects, by at least:
      i) receiving at least one electronic query that at least identifies:
         1) one of more characteristics of a particular population of subjects or objects, and
         2) at least one particular event of at least one particular event type;
      ii) extracting, based on the at least one electronic query, a plurality of population-specific index data structures of the particular population of subjects or objects;
      iii) distributing the plurality of population-specific index data structures of the particular population of subjects or objects into a plurality of searching cluster nodes;
      iv) searching the plurality of searching cluster nodes to identify at least one ontology associated with the at least one particular event of each particular subject or object of the particular population of subjects or objects to form a plurality of longitudinal-personalized data extracts of the at least one particular event of the particular population of subjects or objects; and
      v) generating at least one interactive chronological timeline for each subject or object of the particular population of subjects or objects based on the plurality of longitudinal-personalized data extracts of the at least one particular event of the particular population of subjects or objects and at least one reference event.

2. The system of claim 1, wherein the at least one index data structure is a cohort index data structure.

3. The system of claim 1, wherein, when executing the specialized index generation software, the at least one processor further generates the at least one index data structure by utilizing structure hierarchical data elements of a hierarchical data format.

4. The system of claim 2, wherein the cohort data structure is a tabular structure configured to identify a desired population.

5. The system of claim 1, wherein each property of a plurality of properties of a particular ontology data structure of the respective event are separated by a pre-determined delineator.

6. The system of claim 1,
   wherein the at least one electronic query further identifies the at least one reference event; and
   wherein a date of the at least one reference event defines a reference date for the extracting, based on the at least one electronic query, the plurality of population-specific index data structures of the particular population of subjects or objects.

7. The method of claim 1,
   wherein the at least one electronic query further identifies the at least one reference event; and
   wherein a date of the at least one reference event defines a reference date for the extracting, based on the at least one electronic query, the plurality of population-specific index data structures of the particular population of subjects or objects.

8. A method comprising:
   generating, by at least one processor, at least:
   i) at least one index data structure for a respective event type associated with each respective subject or object; wherein each respective index data structure is a respective event type-specific data schema, defining how to store events of a particular event type to form longitudinal data of each respective subject or object;
   ii) at least one ontology data structure that is configured to describe one or more properties of a respective event of a respective subject or object; wherein the at least one ontology data structure is nested within the at least one index data structure; and
   extracting, by the at least one processor, a respective longitudinal data for a plurality of index data structures and a plurality of ontology data structures associated with a plurality of subjects or objects, by at least:
   i) receiving at least one electronic query that at least identifies:
      1) one of more characteristics of a particular population of subjects or objects, and
      2) at least one particular event of at least one particular event type;
   ii) extracting, based on the at least one electronic query, a plurality of population-specific index data structures of the particular population of subjects or objects;
   iii) distributing the plurality of population-specific index data structures of the particular population of subjects or objects into a plurality of searching cluster nodes;
   iv) searching the plurality of searching cluster nodes to identify at least one ontology associated with the at least one particular event of each particular subject or object of the particular population of subjects or objects to form a plurality of longitudinal-personalized data extracts of the at least one particular event of the particular population of subjects or objects; and v) generating at least one interactive chronological timeline for each subject or object of the particular population of subjects or objects based on the plurality of longitudinal-personalized data extracts of the at least one particular event of the particular population of subjects or objects and at least one reference event.

9. The method of claim 8, wherein the at least one index data structure is a cohort index data structure.

10. The method of claim 8, further comprising:
generating, by the at least one processor, the at least one index data structure by utilizing structure hierarchical data elements of a hierarchical data format.

11. The method of claim 9, wherein the cohort data structure is a tabular structure configured to identify a desired population.

12. The method of claim 8, wherein each property of a plurality of properties of a particular ontology data structure of the respective event are separated by a pre-determined delineator.

* * * * *